United States Patent
Mandro

(10) Patent No.: US 8,066,672 B2
(45) Date of Patent: Nov. 29, 2011

(54) INFUSION PUMP ASSEMBLY WITH A BACKUP POWER SUPPLY

(75) Inventor: Marc A. Mandro, Bow, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 194 days.

(21) Appl. No.: 12/249,540

(22) Filed: Oct. 10, 2008

(65) Prior Publication Data

US 2010/0094220 A1 Apr. 15, 2010

(51) Int. Cl.
*A61M 1/00* (2006.01)
(52) U.S. Cl. .......................... 604/151; 604/67
(58) Field of Classification Search ............... 417/477.2; 600/431–435; 604/65–67, 118–121, 132–147, 604/151–155, 890.1–892.1
See application file for complete search history.

(56) References Cited

U.S. PATENT DOCUMENTS

| | | |
|---|---|---|
| 3,631,847 A | 1/1972 | Hobbs, II |
| 3,692,027 A | 9/1972 | Ellinwood, Jr. |
| 3,752,510 A | 8/1973 | Windischman et al. |
| 3,811,121 A | 5/1974 | Heim et al. |
| 3,811,122 A | 5/1974 | Raber et al. |
| 3,837,339 A | 9/1974 | Aisenberg et al. |
| 3,887,393 A | 6/1975 | La Rue, Jr. |
| 3,951,147 A | 4/1976 | Tucker et al. |
| D248,873 S | 8/1978 | Raitto |
| 4,123,631 A | 10/1978 | Lewis |
| 4,146,029 A | 3/1979 | Ellinwood, Jr. |
| 4,150,672 A | 4/1979 | Whitney et al. |
| D254,446 S | 3/1980 | Raitto |
| 4,206,274 A | 6/1980 | Peels |
| 4,215,701 A | 8/1980 | Raitto |
| 4,267,836 A | 5/1981 | Whitney et al. |
| 4,269,908 A | 5/1981 | Stemme |
| 4,270,532 A | 6/1981 | Franetzki et al. |
| 4,273,121 A | 6/1981 | Jassawalla |
| 4,282,872 A | 8/1981 | Franetzki et al. |
| 4,296,949 A | 10/1981 | Muetterties et al. |

(Continued)

FOREIGN PATENT DOCUMENTS

DE 4329229 A1 3/1995

(Continued)

OTHER PUBLICATIONS

International Search Report and Written Opinion From Corresponding International Application No. PCT/US2007/003490, dated Nov. 28, 2007 (20 pages).

(Continued)

*Primary Examiner* — Nicholas D Lucchesi
*Assistant Examiner* — Gerald Landry, II
(74) *Attorney, Agent, or Firm* — McCormick, Paulding & Huber LLP

(57) ABSTRACT

An infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. A primary power supply is configured to provide primary electrical energy to at least a portion of the processing logic. A backup power supply is configured to provide backup electrical energy to the at least a portion of the processing logic in the event that the primary power supply fails to provide the primary electrical energy to the at least a portion of the processing logic.

23 Claims, 2 Drawing Sheets

U.S. PATENT DOCUMENTS

| | | |
|---|---|---|
| 4,331,262 A | 5/1982 | Snyder et al. |
| 4,371,594 A | 2/1983 | Ohara et al. |
| 4,373,527 A | 2/1983 | Fischell |
| 4,391,883 A | 7/1983 | Williamson et al. |
| 4,392,847 A | 7/1983 | Whitney et al. |
| 4,392,849 A | 7/1983 | Petre et al. |
| 4,395,259 A | 7/1983 | Prestele et al. |
| 4,437,859 A | 3/1984 | Whitehouse et al. |
| 4,443,218 A | 4/1984 | DeCant, Jr. et al. |
| 4,464,170 A | 8/1984 | Clemens et al. |
| 4,469,481 A | 9/1984 | Kobayashi |
| 4,475,901 A | 10/1984 | Kraegen et al. |
| 4,493,704 A | 1/1985 | Beard et al. |
| 4,494,950 A | 1/1985 | Fischell |
| 4,498,843 A | 2/1985 | Schneider et al. |
| 4,533,346 A | 8/1985 | Cosgrove, Jr. et al. |
| 4,542,532 A | 9/1985 | McQuilkin |
| 4,543,093 A | 9/1985 | Christinger |
| 4,550,731 A | 11/1985 | Batina et al. |
| 4,559,037 A | 12/1985 | Franetzki et al. |
| 4,559,038 A | 12/1985 | Berg et al. |
| 4,562,751 A | 1/1986 | Nason et al. |
| 4,596,575 A | 6/1986 | Rosenberg et al. |
| 4,624,661 A * | 11/1986 | Arimond ....................... 604/151 |
| 4,633,878 A | 1/1987 | Bombardieri |
| 4,648,872 A | 3/1987 | Kamen |
| 4,673,396 A | 6/1987 | Urbaniak |
| 4,678,408 A | 7/1987 | Nason et al. |
| 4,685,903 A | 8/1987 | Cable et al. |
| 4,690,878 A | 9/1987 | Nakamura |
| 4,696,671 A | 9/1987 | Epstein et al. |
| 4,731,051 A | 3/1988 | Fischell |
| 4,731,726 A | 3/1988 | Allen, III |
| 4,735,441 A | 4/1988 | Stephens |
| 4,741,731 A | 5/1988 | Starck et al. |
| 4,743,895 A | 5/1988 | Alexander |
| 4,747,828 A | 5/1988 | Tseo |
| 4,790,028 A | 12/1988 | Ramage |
| 4,803,625 A | 2/1989 | Fu et al. |
| 4,804,368 A | 2/1989 | Skakoon et al. |
| 4,809,697 A | 3/1989 | Causey, III et al. |
| 4,826,810 A | 5/1989 | Aoki |
| 4,834,712 A | 5/1989 | Quinn et al. |
| 4,849,852 A | 7/1989 | Mullins |
| 4,856,340 A | 8/1989 | Garrison |
| 4,871,351 A | 10/1989 | Feingold |
| 4,880,712 A | 11/1989 | Gordecki |
| 4,881,063 A | 11/1989 | Fawcett |
| 4,898,578 A | 2/1990 | Rubalcaba, Jr. |
| 4,919,650 A | 4/1990 | Feingold et al. |
| 4,959,640 A | 9/1990 | Hall |
| 4,972,508 A | 11/1990 | King |
| 4,988,337 A | 1/1991 | Ito |
| 4,997,423 A | 3/1991 | Okuda et al. |
| 5,009,646 A | 4/1991 | Sudo et al. |
| 5,019,974 A | 5/1991 | Beckers |
| 5,034,004 A | 7/1991 | Crankshaw |
| 5,049,141 A | 9/1991 | Olive |
| 5,050,612 A | 9/1991 | Matsumura |
| 5,055,830 A | 10/1991 | Cousins et al. |
| 5,063,291 A | 11/1991 | Buehring |
| 5,078,683 A | 1/1992 | Sancoff et al. |
| 5,080,653 A | 1/1992 | Voss et al. |
| 5,088,981 A | 2/1992 | Howson et al. |
| 5,101,814 A | 4/1992 | Palti |
| 5,102,388 A | 4/1992 | Richmond |
| 5,103,216 A | 4/1992 | Sisselman |
| 5,104,374 A | 4/1992 | Bishko et al. |
| 5,150,314 A | 9/1992 | Garratt et al. |
| 5,153,827 A | 10/1992 | Coutré et al. |
| 5,165,407 A | 11/1992 | Wilson et al. |
| 5,174,716 A | 12/1992 | Hora et al. |
| 5,176,502 A | 1/1993 | Sanderson et al. |
| 5,176,644 A | 1/1993 | Srisathapat et al. |
| 5,176,662 A | 1/1993 | Bartholomew et al. |
| 5,181,910 A | 1/1993 | Scanlon |
| 5,187,746 A | 2/1993 | Narisawa |
| 5,191,855 A | 3/1993 | Conforti |
| 5,197,322 A | 3/1993 | Indravudh |
| 5,197,895 A | 3/1993 | Stupecky |
| 5,205,819 A | 4/1993 | Ross et al. |
| 5,216,597 A | 6/1993 | Beckers |
| 5,217,442 A | 6/1993 | Davis |
| 5,248,569 A | 9/1993 | Pine et al. |
| 5,254,093 A | 10/1993 | Bartlett et al. |
| 5,254,096 A | 10/1993 | Rondelet et al. |
| 5,257,971 A | 11/1993 | Lord et al. |
| 5,257,980 A | 11/1993 | Van Antwerp et al. |
| 5,270,702 A | 12/1993 | Krolak |
| 5,290,639 A | 3/1994 | Mallory |
| 5,304,152 A | 4/1994 | Sams |
| 5,307,263 A | 4/1994 | Brown |
| 5,314,416 A | 5/1994 | Lewis et al. |
| 5,317,506 A | 5/1994 | Coutré et al. |
| 5,337,215 A | 8/1994 | Sunderland et al. |
| 5,338,157 A | 8/1994 | Blomquist |
| 5,339,821 A | 8/1994 | Fujimoto |
| 5,341,291 A | 8/1994 | Roizen et al. |
| 5,342,324 A | 8/1994 | Tucker |
| 5,349,852 A | 9/1994 | Kamen et al. |
| 5,350,411 A | 9/1994 | Ryan et al. |
| 5,357,427 A | 10/1994 | Langen et al. |
| 5,364,242 A | 11/1994 | Olsen |
| 5,364,346 A | 11/1994 | Schrezenmeir |
| 5,368,562 A * | 11/1994 | Blomquist et al. .............. 604/65 |
| 5,370,622 A | 12/1994 | Livingston et al. |
| 5,372,133 A | 12/1994 | Hogen Esch |
| 5,376,070 A | 12/1994 | Purvis et al. |
| 5,383,865 A | 1/1995 | Michel |
| 5,389,078 A | 2/1995 | Zalesky et al. |
| 5,390,671 A | 2/1995 | Lord et al. |
| 5,391,157 A | 2/1995 | Harris et al. |
| 5,399,823 A | 3/1995 | McCusker |
| 5,403,648 A | 4/1995 | Chan et al. |
| 5,417,667 A | 5/1995 | Tennican et al. |
| 5,429,602 A | 7/1995 | Hauser |
| 5,433,710 A | 7/1995 | VanAntwerp et al. |
| 5,456,940 A | 10/1995 | Funderburk |
| 5,460,618 A | 10/1995 | Harreld |
| 5,462,525 A | 10/1995 | Srisathapat et al. |
| 5,464,392 A | 11/1995 | Epstein et al. |
| 5,466,218 A | 11/1995 | Srisathapat et al. |
| 5,472,317 A | 12/1995 | Field et al. |
| 5,476,460 A | 12/1995 | Montalvo |
| 5,478,211 A | 12/1995 | Dominiak et al. |
| 5,482,446 A | 1/1996 | Williamson et al. |
| 5,497,772 A | 3/1996 | Schulman et al. |
| 5,505,709 A | 4/1996 | Funderburk et al. |
| 5,507,727 A | 4/1996 | Crainich |
| 5,508,690 A * | 4/1996 | Shur et al. ..................... 340/505 |
| 5,514,097 A | 5/1996 | Knauer |
| 5,514,103 A | 5/1996 | Srisathapat et al. |
| 5,522,803 A | 6/1996 | Teissen-Simony |
| 5,526,844 A | 6/1996 | Kamen et al. |
| 5,527,307 A | 6/1996 | Srisathapat et al. |
| 5,528,359 A | 6/1996 | Taguchi |
| 5,531,697 A | 7/1996 | Olsen et al. |
| 5,531,698 A | 7/1996 | Olsen |
| 5,533,389 A | 7/1996 | Kamen et al. |
| 5,533,996 A | 7/1996 | Murphey et al. |
| 5,538,399 A | 7/1996 | Johnson |
| 5,540,564 A | 7/1996 | Klopfer |
| 5,543,588 A | 8/1996 | Bisset et al. |
| 5,545,140 A | 8/1996 | Conero et al. |
| 5,545,142 A | 8/1996 | Stephens et al. |
| 5,545,143 A | 8/1996 | Fischell |
| 5,545,152 A | 8/1996 | Funderburk et al. |
| 5,558,640 A | 9/1996 | Pfeiler et al. |
| 5,558,641 A | 9/1996 | Glantz et al. |
| 5,562,618 A | 10/1996 | Cai et al. |
| 5,564,915 A | 10/1996 | Johnson |
| 5,567,119 A | 10/1996 | Johnson |
| 5,567,136 A | 10/1996 | Johnson |
| 5,569,026 A | 10/1996 | Novak |
| 5,569,186 A | 10/1996 | Lord et al. |
| 5,569,187 A | 10/1996 | Kaiser |
| 5,573,506 A | 11/1996 | Vasko |

| | | | | | | |
|---|---|---|---|---|---|---|
| 5,575,310 | A | 11/1996 | Kamen et al. | 5,899,855 A | 5/1999 | Brown |
| 5,582,593 | A | 12/1996 | Hultman | 5,913,310 A | 6/1999 | Brown |
| 5,584,813 | A | 12/1996 | Livingston et al. | 5,918,603 A | 7/1999 | Brown |
| 5,593,390 | A | 1/1997 | Castellano et al. | 5,925,021 A | 7/1999 | Castellano et al. |
| 5,594,638 | A | 1/1997 | Iliff | 5,928,196 A | 7/1999 | Johnson et al. |
| 5,609,060 | A | 3/1997 | Dent | 5,928,202 A | 7/1999 | Linnebjerg |
| 5,609,575 | A | 3/1997 | Larson et al. | 5,931,791 A | 8/1999 | Saltzstein et al. |
| 5,613,945 | A | 3/1997 | Cai et al. | 5,933,136 A | 8/1999 | Brown |
| 5,620,312 | A | 4/1997 | Hyman et al. | 5,935,099 A | 8/1999 | Peterson et al. |
| 5,626,144 | A | 5/1997 | Tacklind et al. | 5,935,105 A | 8/1999 | Manning et al. |
| 5,630,710 | A | 5/1997 | Tune et al. | 5,935,106 A | 8/1999 | Olsen |
| 5,632,729 | A | 5/1997 | Cai et al. | 5,940,801 A | 8/1999 | Brown |
| 5,637,095 | A | 6/1997 | Nason et al. | 5,951,521 A | 9/1999 | Mastrototaro et al. |
| 5,637,420 | A | 6/1997 | Jones, Jr. et al. | 5,954,485 A | 9/1999 | Johnson et al. |
| 5,641,892 | A | 6/1997 | Larkins et al. | 5,954,697 A | 9/1999 | Srisathapat et al. |
| 5,643,212 | A | 7/1997 | Coutré et al. | 5,954,700 A | 9/1999 | Kovelman |
| 5,647,853 | A | 7/1997 | Feldmann et al. | 5,956,501 A | 9/1999 | Brown |
| 5,647,854 | A | 7/1997 | Olsen et al. | 5,957,890 A | 9/1999 | Mann et al. |
| 5,651,775 | A | 7/1997 | Walker et al. | 5,960,403 A | 9/1999 | Brown |
| 5,658,133 | A | 8/1997 | Anderson et al. | 5,968,011 A | 10/1999 | Larsen et al. |
| 5,658,250 | A | 8/1997 | Blomquist et al. | 5,971,963 A | 10/1999 | Choi |
| 5,658,252 | A | 8/1997 | Johnson | 5,973,623 A | 10/1999 | Gupta et al. |
| 5,660,176 | A | 8/1997 | Iliff | 5,980,506 A | 11/1999 | Mathiasen |
| 5,665,065 | A | 9/1997 | Colman et al. | 5,989,216 A | 11/1999 | Johnson et al. |
| 5,669,877 | A | 9/1997 | Blomquist | 5,997,476 A | 12/1999 | Brown |
| 5,669,887 | A | 9/1997 | Cooper | 6,007,941 A | 12/1999 | Hermann et al. |
| 5,678,568 | A | 10/1997 | Uchikubo et al. | 6,009,339 A | 12/1999 | Bentsen et al. |
| 5,681,285 | A * | 10/1997 | Ford et al. ............... 604/151 | 6,014,587 A | 1/2000 | Shaw et al. |
| 5,685,844 | A | 11/1997 | Marttila | 6,017,326 A | 1/2000 | Pasqualucci et al. |
| 5,687,734 | A | 11/1997 | Dempsey et al. | 6,017,328 A | 1/2000 | Fischell et al. |
| 5,695,473 | A | 12/1997 | Olsen | 6,024,539 A | 2/2000 | Blomquist |
| 5,704,366 | A | 1/1998 | Tacklind et al. | 6,032,119 A | 2/2000 | Brown et al. |
| 5,713,856 | A * | 2/1998 | Eggers et al. ............... 604/65 | 6,042,565 A | 3/2000 | Hirschman et al. |
| 5,713,857 | A | 2/1998 | Grimard et al. | 6,056,522 A | 5/2000 | Johnson |
| 5,716,725 | A | 2/1998 | Riveron et al. | 6,056,718 A | 5/2000 | Funderburk et al. |
| 5,718,562 | A | 2/1998 | Lawless et al. | 6,059,753 A | 5/2000 | Faust et al. |
| 5,720,729 | A | 2/1998 | Kriesel | 6,063,059 A | 5/2000 | Kriesel |
| 5,727,241 | A | 3/1998 | Yamano et al. | 6,073,036 A | 6/2000 | Heikkinen et al. |
| 5,733,673 | A | 3/1998 | Kunert | 6,077,055 A | 6/2000 | Vilks |
| 5,743,873 | A | 4/1998 | Cai et al. | 6,086,575 A | 7/2000 | Mejslov |
| 5,752,940 | A | 5/1998 | Grimard | 6,090,081 A | 7/2000 | Sudo et al. |
| 5,755,744 | A | 5/1998 | Shaw et al. | 6,093,172 A | 7/2000 | Funderburk et al. |
| 5,762,632 | A | 6/1998 | Whisson | 6,096,011 A | 8/2000 | Trombley, III et al. |
| 5,764,159 | A | 6/1998 | Neftel | 6,099,507 A | 8/2000 | Heinzerling |
| 5,772,409 | A | 6/1998 | Johnson | 6,101,478 A | 8/2000 | Brown |
| 5,772,635 | A | 6/1998 | Dastur et al. | 6,110,152 A | 8/2000 | Kovelman |
| 5,776,116 | A | 7/1998 | Lopez et al. | 6,112,111 A | 8/2000 | Glantz |
| 5,779,665 | A | 7/1998 | Mastrototaro et al. | 6,123,686 A | 9/2000 | Olsen et al. |
| 5,785,681 | A | 7/1998 | Indravudh | 6,123,690 A | 9/2000 | Mejslov |
| 5,788,669 | A | 8/1998 | Peterson | 6,135,949 A | 10/2000 | Russo et al. |
| 5,788,671 | A | 8/1998 | Johnson | 6,165,154 A | 12/2000 | Gray et al. |
| 5,788,673 | A | 8/1998 | Young et al. | 6,171,287 B1 | 1/2001 | Lynn et al. |
| 5,788,678 | A | 8/1998 | Van Antwerp | 6,202,708 B1 | 3/2001 | Bynum |
| 5,795,337 | A | 8/1998 | Grimard | 6,206,856 B1 | 3/2001 | Mahurkar |
| 5,800,387 | A * | 9/1998 | Duffy et al. ............... 604/65 | 6,211,856 B1 | 4/2001 | Choi et al. |
| 5,800,420 | A | 9/1998 | Gross et al. | 6,216,795 B1 * | 4/2001 | Buchl ............... 172/7 |
| 5,801,600 | A | 9/1998 | Butland et al. | 6,225,711 B1 | 5/2001 | Gupta et al. |
| 5,807,336 | A | 9/1998 | Russo et al. | 6,241,704 B1 | 6/2001 | Peterson et al. |
| 5,810,001 | A | 9/1998 | Genga et al. | 6,246,992 B1 | 6/2001 | Brown |
| 5,810,771 | A | 9/1998 | Blomquist | 6,248,093 B1 | 6/2001 | Moberg |
| 5,814,015 | A | 9/1998 | Gargano et al. | 6,253,804 B1 | 7/2001 | Safabash |
| 5,822,715 | A | 10/1998 | Worthington et al. | 6,254,586 B1 | 7/2001 | Mann et al. |
| 5,823,746 | A | 10/1998 | Johnson | 6,259,587 B1 | 7/2001 | Sheldon et al. |
| 5,832,448 | A | 11/1998 | Brown | 6,267,564 B1 | 7/2001 | Rapheal |
| 5,840,020 | A | 11/1998 | Heinonen et al. | 6,269,340 B1 | 7/2001 | Ford et al. |
| 5,840,026 | A | 11/1998 | Uber, III et al. | 6,270,455 B1 | 8/2001 | Brown |
| 5,843,146 | A | 12/1998 | Cross, Jr. | 6,280,416 B1 | 8/2001 | Van Antwerp et al. |
| 5,851,197 | A | 12/1998 | Marano et al. | 6,283,943 B1 | 9/2001 | Dy et al. |
| 5,851,692 | A | 12/1998 | Potts | 6,293,159 B1 | 9/2001 | Kriesel et al. |
| 5,861,018 | A | 1/1999 | Feierbach | 6,293,925 B1 | 9/2001 | Safabash et al. |
| 5,868,669 | A | 2/1999 | Iliff | 6,305,908 B1 | 10/2001 | Hermann et al. |
| 5,871,465 | A | 2/1999 | Vasko | 6,309,375 B1 | 10/2001 | Glines et al. |
| 5,876,370 | A | 3/1999 | Blomquist | 6,311,868 B1 | 11/2001 | Krietemeier et al. |
| 5,879,143 | A | 3/1999 | Cote et al. | 6,321,158 B1 | 11/2001 | DeLorme et al. |
| 5,879,144 | A | 3/1999 | Johnson | 6,362,591 B1 | 3/2002 | Moberg |
| 5,879,163 | A | 3/1999 | Brown et al. | 6,364,859 B1 | 4/2002 | St. Romain et al. |
| 5,882,256 | A | 3/1999 | Shropshire | 6,364,865 B1 | 4/2002 | Lavi et al. |
| 5,885,245 | A | 3/1999 | Lynch et al. | 6,374,876 B2 | 4/2002 | Bynum |
| 5,897,493 | A | 4/1999 | Brown | 6,375,638 B2 | 4/2002 | Nason et al. |

| | | | | | | |
|---|---|---|---|---|---|---|
| 6,416,293 B1 | 7/2002 | Bouchard et al. | | 6,772,650 B2 | 8/2004 | Ohyama et al. |
| 6,422,057 B1 | 7/2002 | Anderson | | 6,800,071 B1 | 10/2004 | McConnell et al. |
| 6,423,035 B1 | 7/2002 | Das et al. | | 6,801,420 B2 | 10/2004 | Talbot et al. |
| 6,427,088 B1 | 7/2002 | Bowman, IV et al. | | 6,805,693 B2 | 10/2004 | Gray et al. |
| 6,428,509 B1 | 8/2002 | Fielder | | 6,810,290 B2 | 10/2004 | Lebel et al. |
| 6,447,481 B1 | 9/2002 | Duchon et al. | | 6,811,533 B2 | 11/2004 | Lebel et al. |
| 6,453,956 B2 | 9/2002 | Safabash | | 6,811,534 B2 | 11/2004 | Bowman, IV et al. |
| 6,458,102 B1 | 10/2002 | Mann et al. | | 6,813,519 B2 | 11/2004 | Lebel et al. |
| 6,459,424 B1 | 10/2002 | Resman | | 6,817,990 B2 | 11/2004 | Yap et al. |
| 6,461,329 B1 | 10/2002 | Van Antwerp et al. | | 6,827,702 B2 | 12/2004 | Lebel et al. |
| 6,461,331 B1 | 10/2002 | Van Antwerp | | 6,830,558 B2 | 12/2004 | Flaherty et al. |
| 6,466,203 B2 | 10/2002 | Van Ee | | 6,835,190 B2 | 12/2004 | Nguyen |
| 6,475,180 B2 | 11/2002 | Peterson et al. | | 6,845,465 B2 | 1/2005 | Hashemi |
| 6,475,196 B1 | 11/2002 | Vachon | | 6,852,104 B2 | 2/2005 | Blomquist |
| 6,485,461 B1 | 11/2002 | Mason et al. | | 6,854,620 B2 | 2/2005 | Ramey |
| 6,485,465 B2 | 11/2002 | Moberg et al. | | 6,872,200 B2 | 3/2005 | Mann et al. |
| 6,520,938 B1 | 2/2003 | Funderburk et al. | | 6,873,268 B2 | 3/2005 | Lebel et al. |
| 6,537,268 B1 | 3/2003 | Gibson et al. | | 6,879,930 B2 | 4/2005 | Sinclair et al. |
| 6,549,423 B1 | 4/2003 | Brodnick | | 6,902,207 B2 | 6/2005 | Lickliter |
| 6,551,276 B1 | 4/2003 | Mann et al. | | 6,916,010 B2 | 7/2005 | Beck et al. |
| 6,551,277 B1 | 4/2003 | Ford | | 6,930,602 B2 | 8/2005 | Villaseca et al. |
| 6,554,798 B1 | 4/2003 | Mann et al. | | 6,932,584 B2 | 8/2005 | Gray et al. |
| 6,554,800 B1 | 4/2003 | Nezhadian et al. | | 6,936,029 B2 | 8/2005 | Mann et al. |
| 6,555,986 B2 | 4/2003 | Moberg | | 6,945,760 B2 | 9/2005 | Gray et al. |
| 6,558,320 B1 | 5/2003 | Causey, III et al. | | 6,950,708 B2 | 9/2005 | Bowman, IV et al. |
| 6,558,351 B1 | 5/2003 | Steil et al. | | 6,951,551 B2 | 10/2005 | Hudon |
| 6,562,001 B2 | 5/2003 | Lebel et al. | | 6,958,705 B2 | 10/2005 | Lebel et al. |
| 6,562,023 B1 | 5/2003 | Marrs et al. | | 6,960,192 B1 | 11/2005 | Flaherty et al. |
| 6,564,105 B2 | 5/2003 | Starkweather et al. | | 6,960,195 B2 | 11/2005 | Heinz et al. |
| 6,571,128 B2 | 5/2003 | Lebel et al. | | 6,964,643 B2 | 11/2005 | Hovland et al. |
| 6,572,542 B1 | 6/2003 | Houben et al. | | 6,974,437 B2 | 12/2005 | Lebel et al. |
| 6,572,586 B1 | 6/2003 | Wojcik | | 6,978,517 B2 | 12/2005 | Collins et al. |
| 6,577,899 B2 | 6/2003 | Lebel et al. | | 6,979,326 B2 | 12/2005 | Mann et al. |
| RE38,189 E | 7/2003 | Walker et al. | | 6,994,619 B2 | 2/2006 | Scholten |
| 6,585,644 B2 | 7/2003 | Lebel et al. | | 6,997,905 B2 | 2/2006 | Gillespie, Jr. et al. |
| 6,585,695 B1 | 7/2003 | Adair et al. | | 6,997,907 B2 | 2/2006 | Safabash et al. |
| 6,591,876 B2 | 7/2003 | Safabash | | 6,997,910 B2 | 2/2006 | Howlett et al. |
| 6,592,551 B1 | 7/2003 | Cobb | | 6,997,920 B2 | 2/2006 | Mann et al. |
| 6,595,756 B2 | 7/2003 | Gray et al. | | 6,997,921 B2 | 2/2006 | Gray et al. |
| 6,607,509 B2 | 8/2003 | Bobroff et al. | | 6,999,854 B2 | 2/2006 | Roth |
| 6,613,015 B2 | 9/2003 | Sandstrom et al. | | 7,011,608 B2 | 3/2006 | Spencer |
| D480,477 S | 10/2003 | Bush et al. | | 7,018,360 B2 | 3/2006 | Flaherty et al. |
| 6,641,533 B2 | 11/2003 | Causey, III et al. | | 7,021,560 B2 | 4/2006 | Gray et al. |
| 6,642,936 B1 | 11/2003 | Engholm et al. | | 7,024,245 B2 | 4/2006 | Lebel et al. |
| 6,645,177 B1 | 11/2003 | Shearn | | 7,025,226 B2 | 4/2006 | Ramey |
| 6,648,821 B2 | 11/2003 | Lebel et al. | | 7,025,743 B2 | 4/2006 | Mann et al. |
| 6,652,493 B1 | 11/2003 | Das | | 7,029,455 B2 | 4/2006 | Flaherty |
| 6,652,510 B2 | 11/2003 | Lord et al. | | 7,029,456 B2 | 4/2006 | Ware et al. |
| 6,656,148 B2 | 12/2003 | Das et al. | | 7,033,338 B2 | 4/2006 | Vilks et al. |
| 6,656,158 B2 | 12/2003 | Mahoney et al. | | 7,033,339 B1 | 4/2006 | Lynn |
| 6,656,159 B2 | 12/2003 | Flaherty | | 7,041,082 B2 | 5/2006 | Blomquist et al. |
| 6,659,948 B2 | 12/2003 | Lebel et al. | | 7,045,361 B2 | 5/2006 | Heiss et al. |
| 6,665,909 B2 | 12/2003 | Collins et al. | | 7,046,230 B2 | 5/2006 | Zadesky et al. |
| 6,669,669 B2 | 12/2003 | Flaherty et al. | | 7,050,927 B2 | 5/2006 | Sinclair et al. |
| 6,684,058 B1 | 1/2004 | Karacaoglu et al. | | 7,052,251 B2 | 5/2006 | Nason et al. |
| 6,685,678 B2 | 2/2004 | Evans et al. | | 7,052,483 B2 | 5/2006 | Wojcik |
| 6,687,546 B2 | 2/2004 | Lebel et al. | | 7,061,140 B2 | 6/2006 | Zhang et al. |
| 6,689,091 B2 | 2/2004 | Bui et al. | | 7,063,684 B2 | 6/2006 | Moberg |
| 6,691,043 B2 | 2/2004 | Ribeiro, Jr. | | 7,066,029 B2 | 6/2006 | Beavis et al. |
| 6,692,457 B2 | 2/2004 | Flaherty | | 7,074,209 B2 | 7/2006 | Evans et al. |
| 6,694,191 B2 | 2/2004 | Starkweather et al. | | 7,075,512 B1 | 7/2006 | Fabre et al. |
| 6,699,218 B2 | 3/2004 | Flaherty et al. | | 7,098,803 B2 | 8/2006 | Mann et al. |
| 6,704,034 B1 | 3/2004 | Rodriguez et al. | | 7,109,878 B2 | 9/2006 | Mann et al. |
| 6,716,195 B2 | 4/2004 | Nolan, Jr. et al. | | 7,115,113 B2 | 10/2006 | Evans et al. |
| 6,723,072 B2 | 4/2004 | Flaherty et al. | | 7,131,967 B2 | 11/2006 | Gray et al. |
| 6,733,446 B2 | 5/2004 | Lebel et al. | | 7,137,964 B2 | 11/2006 | Flaherty |
| 6,740,059 B2 | 5/2004 | Flaherty | | 7,144,384 B2 | 12/2006 | Gorman et al. |
| 6,740,072 B2 | 5/2004 | Starkweather et al. | | 7,146,977 B2 | 12/2006 | Beavis et al. |
| 6,740,075 B2 | 5/2004 | Lebel et al. | | 7,278,983 B2 | 10/2007 | Ireland et al. |
| 6,743,205 B2 | 6/2004 | Nolan, Jr. et al. | | 7,303,549 B2 | 12/2007 | Flaherty et al. |
| 6,744,350 B2 | 6/2004 | Blomquist | | 7,305,984 B2 | 12/2007 | Altobelli et al. |
| 6,749,586 B2 | 6/2004 | Vasko | | 7,306,578 B2 | 12/2007 | Gray et al. |
| 6,749,587 B2 | 6/2004 | Flaherty | | 7,342,660 B2 | 3/2008 | Altobelli et al. |
| 6,752,299 B2 | 6/2004 | Shetler et al. | | 7,498,563 B2 | 3/2009 | Mandro et al. |
| 6,752,785 B2 | 6/2004 | Van Antwerp et al. | | 7,682,338 B2 | 3/2010 | Griffin |
| 6,752,787 B1 | 6/2004 | Causey, III et al. | | 7,927,314 B2 | 4/2011 | Kuracina et al. |
| 6,758,810 B2 | 7/2004 | Lebel et al. | | 2001/0034502 A1 | 10/2001 | Moberg et al. |
| 6,768,425 B2 | 7/2004 | Flaherty et al. | | 2001/0041869 A1 | 11/2001 | Causey, III et al. |
| 6,770,067 B2 | 8/2004 | Lorenzen et al. | | 2001/0056258 A1 | 12/2001 | Evans |

| Publication No. | Date | Inventor |
|---|---|---|
| 2002/0002326 A1 | 1/2002 | Causey, III et al. |
| 2002/0013613 A1 | 1/2002 | Haller et al. |
| 2002/0022807 A1 | 2/2002 | Duchon et al. |
| 2002/0038392 A1 | 3/2002 | De La Huerga |
| 2002/0043951 A1 | 4/2002 | Moberg |
| 2002/0052539 A1 | 5/2002 | Haller et al. |
| 2002/0052574 A1 | 5/2002 | Hochman et al. |
| 2002/0056114 A1 | 5/2002 | Fillebrown et al. |
| 2002/0077852 A1 | 6/2002 | Ford et al. |
| 2002/0082665 A1 | 6/2002 | Haller et al. |
| 2002/0091454 A1 | 7/2002 | Vasko |
| 2002/0107481 A1 | 8/2002 | Reilly et al. |
| 2002/0123672 A1 | 9/2002 | Christophersom et al. |
| 2002/0126036 A1 | 9/2002 | Flaherty et al. |
| 2002/0143290 A1 | 10/2002 | Bui et al. |
| 2002/0158838 A1 | 10/2002 | Smith et al. |
| 2002/0169439 A1 | 11/2002 | Flaherty |
| 2002/0173748 A1 | 11/2002 | McConnell et al. |
| 2002/0193679 A1 | 12/2002 | Malave et al. |
| 2002/0193846 A1 | 12/2002 | Pool et al. |
| 2003/0009133 A1 | 1/2003 | Ramey |
| 2003/0014013 A1 | 1/2003 | Choi |
| 2003/0028079 A1* | 2/2003 | Lebel et al. .................. 600/300 |
| 2003/0028346 A1 | 2/2003 | Sinclair et al. |
| 2003/0065308 A1* | 4/2003 | Lebel et al. ................ 604/891.1 |
| 2003/0076306 A1 | 4/2003 | Zadesky et al. |
| 2003/0088238 A1 | 5/2003 | Poulsen et al. |
| 2003/0114836 A1 | 6/2003 | Estes et al. |
| 2003/0125672 A1 | 7/2003 | Adair et al. |
| 2003/0130618 A1 | 7/2003 | Gray et al. |
| 2003/0132922 A1 | 7/2003 | Philipp |
| 2003/0141981 A1 | 7/2003 | Bui et al. |
| 2003/0161744 A1 | 8/2003 | Vilks et al. |
| 2003/0163089 A1 | 8/2003 | Bynum |
| 2003/0163090 A1 | 8/2003 | Blomquist et al. |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0212364 A1 | 11/2003 | Mann et al. |
| 2003/0212379 A1 | 11/2003 | Bylund et al. |
| 2003/0229311 A1 | 12/2003 | G. Morris et al. |
| 2003/0233069 A1 | 12/2003 | Gillespie, Jr. et al. |
| 2004/0003493 A1 | 1/2004 | Adair et al. |
| 2004/0054326 A1 | 3/2004 | Hommann et al. |
| 2004/0059315 A1 | 3/2004 | Erickson et al. |
| 2004/0064088 A1 | 4/2004 | Gorman et al. |
| 2004/0068230 A1 | 4/2004 | Estes et al. |
| 2004/0073095 A1 | 4/2004 | Causey, III et al. |
| 2004/0073161 A1 | 4/2004 | Tachibana |
| 2004/0082908 A1* | 4/2004 | Whitehurst et al. ............ 604/67 |
| 2004/0082918 A1 | 4/2004 | Evans et al. |
| 2004/0085215 A1 | 5/2004 | Moberg et al. |
| 2004/0092873 A1 | 5/2004 | Moberg |
| 2004/0116893 A1 | 6/2004 | Spohn et al. |
| 2004/0121767 A1 | 6/2004 | Simpson et al. |
| 2004/0127958 A1 | 7/2004 | Mazar et al. |
| 2004/0133166 A1 | 7/2004 | Moberg et al. |
| 2004/0135078 A1 | 7/2004 | Mandro et al. |
| 2004/0140304 A1 | 7/2004 | Leyendecker |
| 2004/0158193 A1 | 8/2004 | Bui et al. |
| 2004/0162528 A1 | 8/2004 | Horvath et al. |
| 2004/0167464 A1 | 8/2004 | Ireland et al. |
| 2004/0172301 A1 | 9/2004 | Mihai et al. |
| 2004/0176667 A1 | 9/2004 | Mihai et al. |
| 2004/0176725 A1 | 9/2004 | Stutz, Jr. et al. |
| 2004/0193090 A1 | 9/2004 | Lebel et al. |
| 2004/0207404 A1 | 10/2004 | Zhang et al. |
| 2004/0235446 A1 | 11/2004 | Flaherty et al. |
| 2004/0243065 A1 | 12/2004 | McConnell et al. |
| 2005/0015056 A1 | 1/2005 | Duchon et al. |
| 2005/0021000 A1 | 1/2005 | Adair et al. |
| 2005/0022274 A1 | 1/2005 | Campbell et al. |
| 2005/0027254 A1 | 2/2005 | Vasko |
| 2005/0035956 A1 | 2/2005 | Sinclair et al. |
| 2005/0048900 A1 | 3/2005 | Scholten |
| 2005/0052429 A1 | 3/2005 | Philipp |
| 2005/0055242 A1 | 3/2005 | Bello et al. |
| 2005/0055244 A1 | 3/2005 | Mullan et al. |
| 2005/0062732 A1 | 3/2005 | Sinclair et al. |
| 2005/0063857 A1 | 3/2005 | Alheidt et al. |
| 2005/0065464 A1* | 3/2005 | Talbot et al. .................... 604/66 |
| 2005/0065817 A1 | 3/2005 | Mihai et al. |
| 2005/0069425 A1 | 3/2005 | Gray et al. |
| 2005/0085760 A1 | 4/2005 | Ware et al. |
| 2005/0096593 A1 | 5/2005 | Pope et al. |
| 2005/0137530 A1 | 6/2005 | Campbell et al. |
| 2005/0137573 A1 | 6/2005 | McLaughlin |
| 2005/0148938 A1 | 7/2005 | Blomquist |
| 2005/0171512 A1 | 8/2005 | Flaherty |
| 2005/0171513 A1 | 8/2005 | Mann et al. |
| 2005/0177111 A1 | 8/2005 | Ozeri et al. |
| 2005/0182366 A1 | 8/2005 | Vogt et al. |
| 2005/0182389 A1 | 8/2005 | LaPorte et al. |
| 2005/0187515 A1 | 8/2005 | Varrichio et al. |
| 2005/0187593 A1 | 8/2005 | Housworth et al. |
| 2005/0192494 A1 | 9/2005 | Ginsberg |
| 2005/0203461 A1 | 9/2005 | Flaherty et al. |
| 2005/0215982 A1 | 9/2005 | Malave et al. |
| 2005/0224705 A1 | 10/2005 | Tobiason et al. |
| 2005/0234404 A1 | 10/2005 | Vilks et al. |
| 2005/0238503 A1 | 10/2005 | Rush et al. |
| 2005/0238507 A1 | 10/2005 | DiIanni et al. |
| 2005/0245904 A1* | 11/2005 | Estes et al. ................. 604/890.1 |
| 2005/0250368 A1 | 11/2005 | Singer et al. |
| 2005/0261660 A1 | 11/2005 | Choi |
| 2005/0263615 A1 | 12/2005 | Kriesel et al. |
| 2005/0267363 A1 | 12/2005 | Duchon et al. |
| 2005/0267550 A1 | 12/2005 | Hess et al. |
| 2005/0267928 A1 | 12/2005 | Anderson et al. |
| 2005/0273059 A1 | 12/2005 | Mernoe et al. |
| 2005/0285880 A1 | 12/2005 | Lai et al. |
| 2006/0016800 A1 | 1/2006 | Paradiso et al. |
| 2006/0025663 A1 | 2/2006 | Talbot et al. |
| 2006/0026535 A1 | 2/2006 | Hotelling et al. |
| 2006/0026536 A1 | 2/2006 | Hotelling et al. |
| 2006/0038791 A1 | 2/2006 | Mackey |
| 2006/0041229 A1 | 2/2006 | Garibotto et al. |
| 2006/0065772 A1 | 3/2006 | Grant et al. |
| 2006/0066581 A1 | 3/2006 | Lyon et al. |
| 2006/0097991 A1 | 5/2006 | Hotelling et al. |
| 2006/0100591 A1 | 5/2006 | Alheidt et al. |
| 2006/0106346 A1 | 5/2006 | Sullivan et al. |
| 2006/0123884 A1* | 6/2006 | Selker et al. .................. 73/24.02 |
| 2006/0129112 A1 | 6/2006 | Lynn |
| 2006/0144942 A1 | 7/2006 | Evans et al. |
| 2006/0160670 A1 | 7/2006 | Spencer |
| 2006/0161870 A1 | 7/2006 | Hotelling et al. |
| 2006/0161871 A1 | 7/2006 | Hotelling et al. |
| 2006/0173406 A1 | 8/2006 | Hayes et al. |
| 2006/0173444 A1 | 8/2006 | Choy et al. |
| 2006/0178633 A1 | 8/2006 | Garibotto et al. |
| 2006/0178836 A1 | 8/2006 | Bai et al. |
| 2006/0184084 A1 | 8/2006 | Ware et al. |
| 2006/0184123 A1 | 8/2006 | Gillespie, Jr. et al. |
| 2006/0184154 A1 | 8/2006 | Moberg et al. |
| 2006/0200257 A1 | 9/2006 | Kirste et al. |
| 2006/0227117 A1 | 10/2006 | Proctor |
| 2006/0229557 A1 | 10/2006 | Fathallah et al. |
| 2006/0232554 A1 | 10/2006 | Wong et al. |
| 2006/0236262 A1 | 10/2006 | Bathiche et al. |
| 2006/0236263 A1 | 10/2006 | Bathiche et al. |
| 2006/0253085 A1 | 11/2006 | Geismar et al. |
| 2006/0264894 A1 | 11/2006 | Moberg et al. |
| 2006/0282290 A1 | 12/2006 | Flaherty et al. |
| 2007/0049870 A1 | 3/2007 | Gray et al. |
| 2007/0060872 A1 | 3/2007 | Hall et al. |
| 2007/0066956 A1 | 3/2007 | Finkel |
| 2007/0093750 A1 | 4/2007 | Jan et al. |
| 2007/0112298 A1* | 5/2007 | Mueller et al. .................. 604/65 |
| 2007/0118405 A1 | 5/2007 | Campbell et al. |
| 2007/0161955 A1 | 7/2007 | Bynum et al. |
| 2007/0167905 A1 | 7/2007 | Estes et al. |
| 2007/0178776 A1 | 8/2007 | Etter et al. |
| 2007/0191770 A1 | 8/2007 | Moberg et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |

| | | | |
|---|---|---|---|
| 2007/0255250 A1 | 11/2007 | Moberg et al. | |
| 2007/0258395 A1 | 11/2007 | Jollota et al. | |
| 2008/0009824 A1 | 1/2008 | Moberg et al. | |
| 2008/0051710 A1 | 2/2008 | Moberg et al. | |
| 2008/0051711 A1 | 2/2008 | Mounce et al. | |
| 2008/0097321 A1 | 4/2008 | Mounce et al. | |
| 2008/0097328 A1 | 4/2008 | Moberg et al. | |
| 2008/0125701 A1* | 5/2008 | Moberg et al. | 604/67 |
| 2008/0160492 A1 | 7/2008 | Campbell et al. | |
| 2008/0161754 A1 | 7/2008 | Marano-Ford | |
| 2008/0177900 A1 | 7/2008 | Grant et al. | |
| 2009/0036870 A1 | 2/2009 | Mounce et al. | |
| 2009/0062767 A1 | 3/2009 | Van Antwerp et al. | |
| 2009/0062778 A1* | 3/2009 | Bengtsson et al. | 604/890.1 |
| 2009/0069749 A1 | 3/2009 | Miller et al. | |
| 2009/0099523 A1 | 4/2009 | Grant et al. | |
| 2009/0164251 A1 | 6/2009 | Hayter | |
| 2009/0171291 A1 | 7/2009 | Bente, IV et al. | |
| 2009/0234213 A1 | 9/2009 | Hayes et al. | |
| 2009/0259217 A1 | 10/2009 | Hyde et al. | |
| 2009/0270811 A1 | 10/2009 | Mounce et al. | |

FOREIGN PATENT DOCUMENTS

| | | |
|---|---|---|
| DE | 19627619 A1 | 1/1998 |
| DE | 20110059 A1 | 8/2002 |
| EP | 0256694 A1 | 2/1988 |
| EP | 0258566 A2 | 3/1988 |
| EP | 0338671 A1 | 10/1989 |
| EP | 0398394 A2 | 11/1990 |
| EP | 0554995 B1 | 8/1993 |
| EP | 0749757 A2 | 12/1996 |
| EP | 0763368 A2 | 3/1997 |
| EP | 0806738 A1 | 11/1997 |
| EP | 0830597 B1 | 3/1998 |
| EP | 1007137 B1 | 6/2000 |
| EP | 1109586 B1 | 6/2001 |
| EP | 1177802 A1 | 2/2002 |
| EP | 1338295 A1 | 8/2003 |
| EP | 1473050 A1 | 3/2004 |
| EP | 1115435 B1 | 8/2005 |
| EP | 1347705 B1 | 12/2005 |
| EP | 1688085 A1 | 8/2006 |
| EP | 1839694 A1 | 10/2007 |
| GB | 2218831 A | 11/1989 |
| WO | 94/08647 A1 | 4/1994 |
| WO | 95/24229 A2 | 9/1995 |
| WO | 95/28878 A1 | 11/1995 |
| WO | 95/31233 A1 | 11/1995 |
| WO | 96/08281 A1 | 3/1996 |
| WO | 96/14100 A1 | 5/1996 |
| WO | 96/20745 A1 | 7/1996 |
| WO | 96/36389 A1 | 11/1996 |
| WO | 97/21456 A1 | 6/1997 |
| WO | 97/40482 A1 | 10/1997 |
| WO | 98/14234 A1 | 4/1998 |
| WO | 98/17336 A1 | 4/1998 |
| WO | 98/20439 A1 | 5/1998 |
| WO | 98/24358 A2 | 6/1998 |
| WO | 98/42407 A1 | 10/1998 |
| WO | 98/49659 A2 | 11/1998 |
| WO | 98/58693 A1 | 12/1998 |
| WO | 98/59487 A1 | 12/1998 |
| WO | 99/08183 A1 | 2/1999 |
| WO | 99/10801 A1 | 3/1999 |
| WO | 99/18532 A1 | 4/1999 |
| WO | 99/22236 A1 | 5/1999 |
| WO | 99/44655 A2 | 9/1999 |
| WO | 99/59663 A1 | 11/1999 |
| WO | 00/10628 A2 | 3/2000 |
| WO | 00/28217 A1 | 5/2000 |
| WO | 00/69493 A1 | 11/2000 |
| WO | 01/00261 A1 | 1/2001 |
| WO | 01/61616 A3 | 8/2001 |
| WO | 01/70304 A1 | 9/2001 |
| WO | 02/04047 A2 | 1/2002 |
| WO | 02/49509 A2 | 6/2002 |
| WO | 02/053220 A2 | 7/2002 |
| WO | 02/056945 A2 | 7/2002 |
| WO | 02/070049 A1 | 9/2002 |
| WO | 02/083209 A1 | 10/2002 |
| WO | 03/053498 A2 | 7/2003 |
| WO | 03/059422 A1 | 7/2003 |
| WO | 03/063932 A2 | 8/2003 |
| WO | 03/071930 A2 | 9/2003 |
| WO | 03/090838 A1 | 11/2003 |
| WO | 03/094075 A1 | 11/2003 |
| WO | 2004/007133 A1 | 1/2004 |
| WO | 2004/008956 A2 | 1/2004 |
| WO | 2004/009160 A1 | 1/2004 |
| WO | 2004028596 A1 | 4/2004 |
| WO | 2004/058327 A2 | 7/2004 |
| WO | 2004/069095 A2 | 8/2004 |
| WO | 2004/070548 A2 | 8/2004 |
| WO | 2004/070557 A2 | 8/2004 |
| WO | 2004/070994 A2 | 8/2004 |
| WO | 2004/070995 A2 | 8/2004 |
| WO | 2004/098390 A2 | 11/2004 |
| WO | 2005/000378 A2 | 1/2005 |
| WO | 2005/010796 A2 | 2/2005 |
| WO | 2005/016411 A2 | 2/2005 |
| WO | 2005/019766 A2 | 3/2005 |
| WO | 2005/019987 A2 | 3/2005 |
| WO | 2005/039671 A2 | 5/2005 |
| WO | 2005/094920 A1 | 10/2005 |
| WO | 2005/101279 A2 | 10/2005 |
| WO | 2005-102416 A1 | 11/2005 |
| WO | 2005/112899 A2 | 12/2005 |
| WO | 2005/121938 A2 | 12/2005 |
| WO | 2006/001929 A1 | 1/2006 |
| WO | 2006/023147 A2 | 3/2006 |
| WO | 2006/032652 A1 | 3/2006 |
| WO | 2006/081975 A1 | 8/2006 |
| WO | 2006/083831 A1 | 8/2006 |
| WO | 2006/097453 A1 | 9/2006 |
| WO | 2006/108809 A1 | 10/2006 |
| WO | 2007/016145 A1 | 2/2007 |

OTHER PUBLICATIONS

International Search Report and Written Opinion From Corresponding International Application No. PCT/US2007/003567, dated Oct. 17, 2007 (18 pages).

International Search Report and Written Opinion From Corresponding International Application No. PCT/US2007/003587, Nov. 12, 2007 (18 pages).

International Search Report and Written Opinion From Corresponding International Application No. PCT/US2007/003634, Oct. 2, 2007 (18 pages).

International Search Report From Corresponding International Application No. PCT/US2009/060158, dated Mar. 23, 2010 (7 pages).

International Search Report and Written Opinion From Corresponding International Application No. PCT/US2009/093169, dated Mar. 31, 2010 (23 pages).

International Preliminary Report on Patentability From Corresponding International Application No. PCT/US2007/003567, dated Aug. 21, 2008 (11 pages).

Extended European Search Report From European Application No. 09075460.7, dated Mar. 5, 2010 (14 pages).

Office Action from Japanese Appln. No. 2002-591067 dated Jun. 10, 2008 (4 pages).

Non-final Office Action from corresponding U.S. Appl. No. 12/249,891, dated Nov. 18, 2009 (15 pages).

Conical fittings with a 6% (Luer) taper for syringes, needles and certain other medical equipment—Lock fittings, British Standard, BS EN 1707 : 1997 (20 pages).

Conical fittings with a 6% (Luer) taper for syringes, needles and certain other medical equipment, Part 1. General requirements, British Standard, BS EN 20594-1 : 1994 ISO 594-1 : 1986 (17 pages).

* cited by examiner

INFUSION PUMP ASSEMBLY WITH A BACKUP POWER SUPPLY

TECHNICAL FIELD

This disclosure relates to infusion pump assemblies and, more particularly, to infusion pump assemblies that include redundant power supplies.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impractically expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

Unfortunately, the failure of the power supply included within the infusion pump assembly may result in the infusion pump assembly ceasing to operate. Further, as the infusion pump assembly is no longer operating, the user may not be warned of the failure of the infusion pump assembly.

SUMMARY OF DISCLOSURE

In a first implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. A primary power supply is configured to provide primary electrical energy to at least a portion of the processing logic. A backup power supply is configured to provide backup electrical energy to the at least a portion of the processing logic in the event that the primary power supply fails to provide the primary electrical energy to the at least a portion of the processing logic.

One or more of the following features may be included. The primary power supply may include a first battery. The backup power supply may be a super capacitor assembly.

The processing logic may include one or more circuit partitioning components configured to divide the processing logic into primary processing logic and backup processing logic. The primary processing logic may include a primary microprocessor. The backup processing logic may include a safety microprocessor. The one or more circuit partitioning components may include one or more of a diode assembly and a current limiting assembly.

The diode assembly may be configured to allow the primary power supply to charge the backup power supply while prohibiting the backup power supply from providing backup electrical energy to the primary processing logic in the event that the primary power supply fails to provide the primary electrical energy to the primary processing logic. The current limiting assembly may be configured to limit the amount of the primary electrical energy available to charge the backup power supply.

The primary power supply may be configured to provide electrical energy to one or more subsystems included within the infusion pump assembly. The primary power supply and the backup power supply may be configured to provide electrical energy to an audio system included within the infusion pump assembly. The audio system may be configured to provide an escalating alarm sequence in the event of a loss of a beacon signal. The escalating alarm sequence may include at least a low-intensity alarm and a high-intensity alarm.

In another implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. A first battery is configured to provide primary electrical energy to at least a portion of the processing logic. A super capacitor assembly is configured to provide backup electrical energy to the at least a portion of the processing logic in the event that the first battery fails to provide the primary electrical energy to the at least a portion of the processing logic.

One or more of the following features may be included. The processing logic may include one or more circuit partitioning components configured to divide the processing logic into primary processing logic and backup processing logic. The primary processing logic may include a primary microprocessor. The backup processing logic may include a safety microprocessor. The one or more circuit partitioning components may include one or more of a diode assembly and a current limiting assembly.

In another implementation, an infusion pump assembly includes a reservoir assembly configured to contain an infusible fluid. A motor assembly is configured to act upon the reservoir assembly and dispense at least a portion of the infusible fluid contained within the reservoir assembly. Processing logic is configured to control the motor assembly. A primary power supply is configured to provide primary electrical energy to at least a portion of the processing logic. A backup power supply is configured to provide backup electrical energy to the at least a portion of the processing logic in the event that the primary power supply fails to provide the primary electrical energy to the at least a portion of the processing logic. The processing logic includes one or more circuit partitioning components configured to divide the processing logic into primary processing logic and backup processing logic.

One or more of the following features may be included. The primary power supply may include a first battery. The backup power supply may be a super capacitor assembly. The primary processing logic may include a primary microprocessor. The backup processing logic may include a safety microprocessor.

The one or more circuit partitioning components may include one or more of a diode assembly and a current limiting assembly. The diode assembly may be configured to allow the primary power supply to charge the backup power supply while prohibiting the backup power supply from providing backup electrical energy to the primary processing logic in the event that the primary power supply fails to provide the primary electrical energy to the primary processing logic.

In another implementation, an alarm system includes processing logic configured to generate an alarm control signal. An RS232 line driver circuit is coupled to the processing logic and configured to receive the alarm control signal and generate an alarm output signal based, at least in part, upon the alarm control signal. An audio driver assembly is coupled to the RS232 line driver circuit and configured to receive the alarm output signal and generate an audible alarm signal based, at least in part, upon the alarm output signal.

One or more of the following features may be included. The audio driver assembly may include a Piezo electric diaphragm. The alarm system may be included within an infusion pump assembly. The infusion pump assembly may include a reservoir assembly configured to contain an infusible fluid. A motor assembly may be configured to act upon the reservoir assembly and dispense at least a portion of the infusible fluid contained within the reservoir assembly. A primary power supply may be configured to provide primary electrical energy to at least a portion of the processing logic. A backup power supply may be configured to provide backup electrical energy to the at least a portion of the processing logic in the event that the primary power supply fails to provide the primary electrical energy to the at least a portion of the processing logic. The processing logic may be further configured to control the motor assembly.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
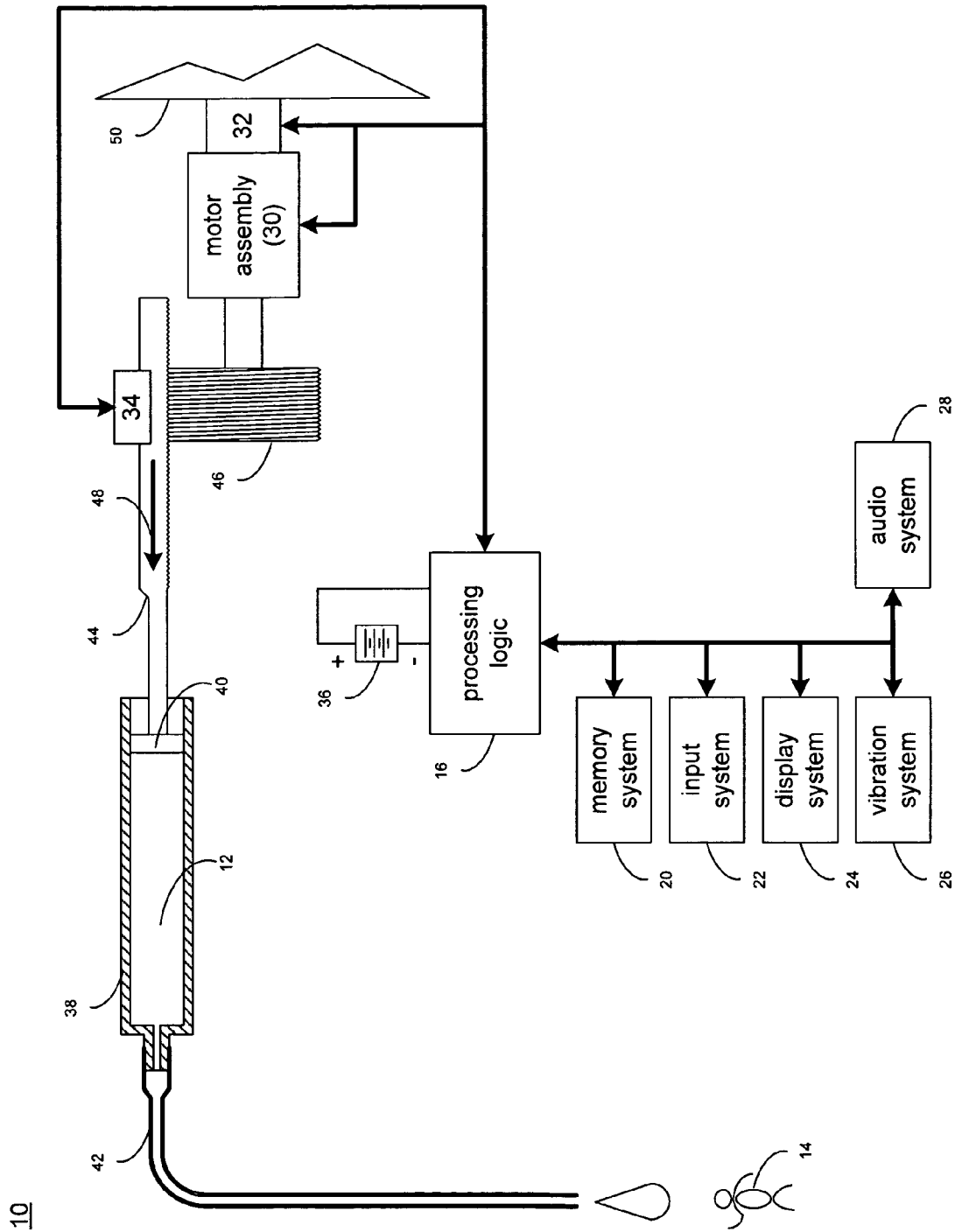
FIG. 1 is a diagrammatic view of an infusion pump assembly including processing logic.

Referring to FIG. 1, there is shown infusion pump assembly 10 that may be configured to deliver infusible fluid 12 to user 14. As discussed above, infusible fluid 12 may be delivered intravenously (i.e., into a vein), subcutaneously (i.e., into the skin), arterially (i.e., into an artery), and epidurally (i.e., into the epidural space). Examples of infusible fluid 12 may include but are not limited to insulin, nutrients, saline solution, antibiotics, analgesics, anesthetics, hormones, vasoactive drugs, and chelation drugs Infusion pump assembly 10 may include processing logic 16 that executes one or more processes that may be required for infusion pump assembly 10 to operate properly. Processing logic 16 may include one or more microprocessors (to be discussed below in greater detail), one or more input/output controllers (not shown), and cache memory devices (not shown). One or more data buses and/or memory buses may be used to interconnect processing logic 16 with one or more subsystems.

Examples of such subsystems may include but are not limited to memory system 20, input system 22, display system 24, vibration system 26, audio system 28, motor assembly 30, force sensor 32, and displacement detection device 34. Infusion pump assembly 10 may include primary power supply 36 (e.g. a first battery) for providing electrical power to at least a portion of processing logic 16 and one or more of the subsystems (e.g., memory system 20, input system 22, display system 24, vibration system 26, audio system 28, motor assembly 30, force sensor 32, and displacement detection device 34).

Infusion pump assembly 10 may include reservoir assembly 38 configured to contain infusible fluid 12. In some embodiments, reservoir assembly 38 may be a reservoir assembly similar to that described in U.S. Patent Application Publication No. US 2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include, but is not limited to: a barrel with a plunger, a cassette or container at least partially constructed of a flexible membrane.

Plunger assembly 40 may be configured to displace infusible fluid 12 from reservoir assembly 38 through cannula assembly 42 so that infusible fluid 12 may be delivered to user 14. In this particular embodiment, plunger assembly 40 is shown to be displaceable by partial nut assembly 44, which may engage lead screw assembly 46 that may be rotatable by motor assembly 30 in response to signals received from processing logic 16. An example of partial nut assembly 44 may include but is not limited to a nut assembly that is configured to wrap around lead screw assembly 46 by e.g., 30 degrees. In some embodiments, the pump assembly may be similar to one described in U.S. Pat. No. 7,306,578, issued Dec. 11, 2007, which is herein incorporated by reference in its entirety. For example, in some embodiments, the infusion pump assembly 10 may include a housing that contains the components needed to cause the reservoir assembly 38 to deliver medication to a user, including the reservoir assembly 38, the motor assembly 30, processing logic 16, primary power supply 36 and backup power supply 108.

During operation of infusion pump assembly 10, infusible fluid 12 may be delivered to user 14 in accordance with e.g. a defined delivery schedule. For illustrative purposes only, assume that infusion pump assembly 10 is configured to provide 0.00025 mL of infusible fluid 12 to user 14 every three minutes. Accordingly, every three minutes, processing logic 16 may provide power to motor assembly 30 to allow motor assembly 30 to rotate lead screw assembly 46 the appropriate amount so that partial nut assembly 44 (and therefore plunger assembly 40) may be displaced the appropriate amount in the direction of arrow 48 so that 0.00025 mL of infusible fluid 12 are provided to user 14 (via cannula 42). It should be understood that the volume of infusible fluid 12 that may be provided to user 14 may vary based upon, at least in part, the nature of the infusible fluid (e.g., the type of fluid, concentration, etc.), use parameters (e.g., treatment type, dosage, etc.), as well as various other factors that will be understood by one having skill in the art. As such, the foregoing illustrative example should not be construed as a limitation of the present disclosure.

Force sensor 32 may be configured to provide processing logic 16 with data concerning the force required to drive plunger assembly 40 into reservoir assembly 38. Force sensor 32 may include one or more strain gauges and/or pressure sensing gauges and may be positioned between motor assembly 30 and an immovable object (e.g. bracket assembly 50) included within infusion pump assembly 10.

In one embodiment, force sensor 32 includes four strain gauges (not shown), such that: two of the four strain gauges are configured to be compressed when driving plunger 40 into reservoir assembly 38; and two of the four strain gauges are configured to be stretched when driving plunger 40 into reservoir assembly 38. The four strain gauges (not shown) may be connected to a Wheatstone Bridge (not shown) that produces an analog force signal (not shown) that is a function of the pressure sensed by force sensor 32. The analog force signal (not shown) produced by force sensor 32 may be provided to an analog-to-digital converter (not shown) that may convert the analog force signal (not shown) into a digital force signal (not shown) that may be provided to processing logic 16. An amplifier assembly (not shown) may be positioned prior to the above-described analog-to-digital converter and may be configured to amplify the output of e.g., force sensor 32 to a level sufficient to be processed by the above-described analog-to-digital converter.

Motor assembly 30 may be configured as e.g., a brush-type DC electric motor. Further, motor assembly 30 may include a reduction gear assembly (not shown) that e.g. requires motor assembly 30 to rotate e.g., three-thousand revolutions for each revolution of lead screw assembly 42, thus increasing the torque and resolution of motor assembly 30 by a factor of three-thousand.

Figure 2:
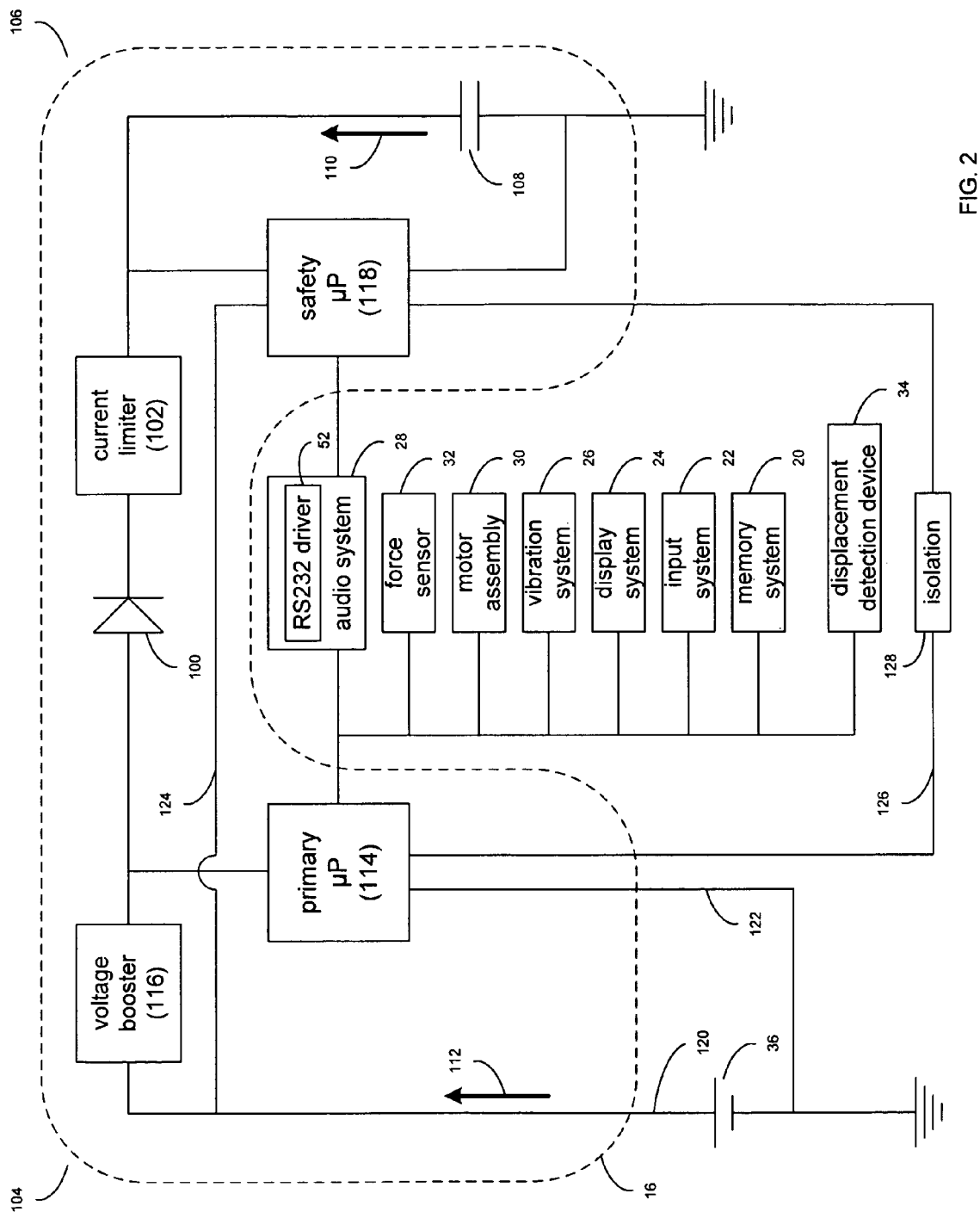
FIG. 2 is a more-detailed diagrammatic view of the processing logic of FIG. 1.

Referring also to FIG. 2, there is shown a more-detailed diagrammatic view of processing logic 16. Processing logic 16 may include one or more circuit partitioning components 100, 102 configured to divide processing logic 16 into primary processing logic 104 and backup processing logic 106. Examples of one or more circuit partitioning components 100, 102 may include but are not limited to diode assembly 100 and current limiting assembly 102.

Diode assembly 100 may be configured to allow primary power supply 36 to charge backup power supply 108 included within backup processing logic 106, while prohibiting backup power supply 108 from providing backup electrical energy 110 to primary processing logic 104 in the event that some form of failure prevents primary power supply 36 from providing primary electrical energy 112 to primary processing logic 104. An example of backup power supply 108 may include but is not limited to a super capacitor assembly. An example of such a super capacitor assembly may include but is not limited to a electric double-layer capacitor manufactured by Elna Co. Ltd. of Yokohama, Japan.

Current limiting assembly 102 may be configured to limit the amount of primary electrical energy 112 available to charge backup power supply 108. Specifically, as primary power supply 36 may be configured to charge backup power supply 108, the amount of current available from primary power supply 36 may be limited to e.g., avoid depriving primary processing logic 104 of a requisite portion of primary electrical energy 112.

Primary processing logic 104 may include primary microprocessor 114 and voltage booster circuit 116. An example of primary microprocessor 114 may include but is not limited to a H8S/2000 manufactured by Renesas Technology America Inc. of San Jose, Calif. Voltage booster circuit 116 may be configured to increase the voltage potential of primary electrical energy 112 provided by primary power supply 36 to a level sufficient to power primary microprocessor 114. An example of voltage booster circuit 116 may include but is not limited to a LTC3421 manufactured by Linear Technology of Milpitas, Calif.

Current limiting assembly 102 may be configured to limit the amount of current available to charge backup power supply 108 during the power-up of primary microprocessor 114. Specifically and for illustrative purposes, current limiter assembly 102 may be controlled by primary microprocessor 114 and current limiting assembly 102 may be disabled (i.e., provide no charging current to backup power supply 108) until after primary microprocessor 114 is fully powered up. Upon primary microprocessor 114 being fully powered up, primary microprocessor 114 may now enable current limiting assembly 102, thus providing charging current to backup power supply 108. Alternatively and upon being initially energized, current limiting assembly 102 may be configured to prohibit the flow of charging current to backup power supply 108 for a time sufficient to allow for the powering up of primary microprocessor 114.

Backup processing logic 106 may include backup power supply 108 and safety microprocessor 118. An example of safety microprocessor 118 may include but is not limited to a MSP430 manufactured by Texas Instruments of Dallas, Tex.

Primary power supply 36 may be configured to provide primary electrical energy 112 to at least a portion of processing logic 16. Specifically and during normal operation of infusion pump assembly 10, primary power supply 36 may be configured to provide primary electrical energy 112 to all of processing logic 16 (including the various components of primary processing logic 104 and backup processing logic 106), as well as various subsystems included within infusion pump assembly 10.

Examples of such subsystems may include but are not limited to memory system 20, input system 22, display system 24, vibration system 26, audio system 28, motor assembly 30, force sensor 32, and displacement detection device 34.

Backup power supply 108 may be configured to provide backup electrical energy 110 to the at least a portion of processing logic 16 in the event that primary power supply 36 fails to provide primary electrical energy 112 to at least a portion of processing logic 16. Specifically, in the event that primary power supply 36 fails and, therefore, can no longer provide primary electrical energy 112 to processing logic 16, backup power supply 108 may be configured to provide backup electrical energy 110 to backup processing logic 106.

For illustrative purposes only, assume that infusion pump assembly 10 is operating normally and primary power supply 36 is providing primary electrical energy 112 to processing logic 16. As discussed above, voltage booster circuit 116 may increase the voltage potential of primary electrical energy 112 to a level sufficient to power primary microprocessor 114, wherein voltage booster circuit 116 and primary microprocessor 114 are both included within primary processing logic 104.

Further, diode assembly 100 may allow a portion of primary electrical energy 112 to enter backup processing logic 106, thus enabling the operation of safety microprocessor 118 and the charging of backup power supply 108. As discussed above an example of backup power supply 108 may include but is not limited to a super capacitor. As discussed above, current limiter assembly 102 may limit the quantity of current provided by primary power supply 36 to backup processing logic 106, thus preventing the diversion of too large a portion of primary electrical energy 112 from primary processing logic 104 to backup processing logic 106.

Accordingly, in addition to powering safety microprocessor 118, primary power supply 36 may charge backup power supply 108. In a preferred embodiment, backup power supply 108 is a 0.33 farad super capacitor.

Safety microprocessor 118 may monitor the status of primary power supply 36 by monitoring the voltage potential present at the input of voltage booster circuit 116. Alternatively, safety microprocessor 118 may monitor the status of primary power supply 36 by e.g. monitoring (via conductor 124) the voltage potential present at the output of voltage booster circuit 116. Further still, safety microprocessor 118 and primary microprocessor 114 may be electrically-coupled via e.g. conductor 126 and primary microprocessor 114 may be configured to continuously provide a "beacon" signal to safety microprocessor 118. Conductor 126 may include isolation circuit 128 (e.g., one or more diodes assemblies) to electrically isolate safety microprocessor 118 and primary microprocessor 114. Accordingly, provided safety microprocessor 118 continues to receive the "beacon" signal from primary microprocessor 114, primary microprocessor 114 is functioning and, therefore, being properly powered by primary power supply 36. In the event that safety microprocessor 118 fails to receive the "beacon" signal from primary microprocessor 114, an alarm sequence may be initiated.

Further still, safety microprocessor 118 may be configured to continuously provide a "beacon" signal to primary microprocessor 114. Accordingly, provided primary microprocessor 114 continues to receive the "beacon" signal from safety microprocessor 118, safety microprocessor 118 is functioning and, therefore, being properly powered by backup power supply 108. In the event that primary microprocessor 114 fails to receive the "beacon" signal from safety microprocessor 118, an alarm sequence may be initiated.

As used in this disclosure, a "beacon" signal may be considered an event that is performed by primary microprocessor 114 (and/or safety microprocessor 118) solely for the purpose of making the presence of primary microprocessor 114 (and/or safety microprocessor 118) known. Additionally/alternatively, the "beacon" signal may be considered an event that is performed by primary microprocessor 114 (and/or safety microprocessor 118) for the purpose of performing a task, wherein the execution of this event is monitored by safety microprocessor 118 (and/or primary microprocessor 114) to confirm the presence of primary microprocessor 114 (and/or safety microprocessor 118).

Assume for illustrative purposes that primary power supply 36 fails. For example, assume that primary power supply 36 physically fails (as opposed to simply becoming discharged). Examples of such a failure may include but are not limited to the failing of a cell (not shown) within primary power supply 36 and the failing of a conductor (e.g., one or more of conductors 120, 122) that electrically-couples primary power supply 36 to processing logic 16. Accordingly, in the event of such a failure, primary power supply 36 may no longer provide primary electrical energy 112 to processing logic 16.

However, when such a failure of primary power supply 36 occurs, the voltage potential present at the output of voltage booster circuit 116 and the voltage potential present at the input of voltage booster circuit 116 may be reduced to zero. Since safety microprocessor 118 may monitor (as discussed above) one or more of these voltage potentials, safety microprocessor 118 may be knowledgeable that primary power supply 36 has failed.

Further, when such a failure of primary power supply 36 occurs, primary microprocessor 114 will no longer be powered and, therefore, primary microprocessor 114 will no longer produce the above-described "beacon" signals. Since safety microprocessor 118 monitors the above-described "beacon" signals, safety microprocessor 118 may be knowledgeable that primary power supply 36 has failed.

As discussed above, in the event of such a failure of primary power supply 36, as diode assembly 100 is reversed-biased, backup power supply 108 may not provide backup electrical energy 110 to primary processing logic 104. Accordingly, primary processing logic 104 will know longer function.

Upon sensing the failure of primary power supply 36, safety microprocessor 118 may initiate an alarm sequence that may result in audio system 28 being energized. Audio system 28 may be controllable by both safety microprocessor 118 and primary microprocessor 114. Alternatively, a separate audio system may be used for each of safety microprocessor 118 and primary microprocessor 114. Audio system 28 may include a Piezo electric diaphragm, an example of which may include but is not limited to a 7BB-15-6 manufactured by Murata of Kyoto, Japan Audio system 28 may further include an RS232 line driver circuit 52, such as a MAX3319/MAX3221 manufactured by Maxim Integrated Products of Sunnyvale, Calif. One or more of primary microprocessor 114 and safety microprocessor 118 may be configured to provide an alarm control signal (e.g., a square wave; not shown) to RS232 line driver circuit 52 to generate an alarm output signal (not shown) that may be provided to and may drive the above-described Piezo electric diaphragm.

The alarm sequence initiated by safety microprocessor 118 is intended to inform user 14 of the failure of primary power supply 36 so that user 14 may take the appropriate action (e.g. seeking an alternative means to have their therapy performed and/or having infusion pump assembly 10 repaired/replaced). Backup power supply 108 may be sized so that safety microprocessor 118 and audio system 28 may continue to function for up to fifteen minutes or more after the failure of primary power supply 36 (i.e., depending on design specifications).

The alarm sequence initiated by safety microprocessor 118 and primary microprocessor 114 may be an "escalating" alarm sequence in some embodiments. For example, at first a discreet "vibrating" alarm may be initiated (via vibration system 26). In the event that this "vibrating" alarm is not acknowledged within a defined period of time (e.g., one minute), a low volume audible alarm may be initiated. In the event that this low volume alarm is not acknowledged within a defined period of time (e.g., one minute), a medium volume audible alarm may be initiated. In the event that this medium volume alarm is not acknowledged within a defined period of time (e.g., one minute), a high volume audible alarm may be initiated. The escalating alarm sequence may provide a notification to user 14, in which the notification may be discreet or less disruptive at the onset. The initially discreet or less disruptive notification may be advantageous as user 14 may experience minimal disruption. However, in the event that user 14 does not acknowledge the alarm, the escalating nature of the alarm may provide for additional layers of safety to user 14. Additionally, in a case of audio system 28 error, or vibration system 26 error, the escalating alarm sequence, which may include both vibration and audio alarms, may insure that user 14 may be notified regardless of whether both systems 26, 28 are functioning.

Audio system 28, in some embodiments, may be configured to perform a self test upon power up. For example, upon infusion pump assembly 10 being initially powered up, audio system 28 may provide a "beep-type" signal to each sound generating device included within audio system 28. In the event that user 14 does not hear these "beep-type" signal(s), user 14 may take the appropriate action (e.g. seeking an alternative means to have their therapy performed and/or having infusion pump assembly 10 repaired/replaced). As discussed above, audio system 28 may be controllable by safety microprocessor 118 and/or primary micro-processor 114. Accordingly, when performing the above-described self test upon power up, safety microprocessor 118 and/or primary microprocessor 114 may control the above-described self test. This feature may provide for additional safety to user 14, as user 14 may be alerted to a system error earlier than may otherwise be the case. Thus, a method may be provided to notify the user early of system errors. Also, the system may otherwise not be aware of an error in audio system 28, thus, this feature provides for identification of a failure by user 14 that may otherwise go undetected.

During the failure of primary power supply 36, safety microprocessor 118 may continue to monitor the voltage potential present at the output of voltage booster circuit 116 and/or the voltage potential present at the input of voltage booster circuit 116. Additionally, safety microprocessor 118 may continue to monitor for the presence of the above-described "beacon" signals. Accordingly, in the event that the failure of primary power supply 36 was a temporary event (e.g. primary power supply 36 is an out-of-date battery and is being replaced with a new battery), safety microprocessor 118 may be knowledgeable when primary power supply 36 is once again functioning properly.

Upon primary power supply 36 once again functioning properly, diode assembly 100 and current limiting assembly 102 may allow a portion of primary electrical energy 112 produced by primary power supply 36 to recharge backup power supply 108.

Additionally, safety microprocessor 118 and primary microprocessor 114 may each maintain a real-time clock, so that the various doses of infusible fluid may be dispensed at the appropriate time of day. As primary microprocessor 114 was not functioning during the failure of primary power supply 36, the real-time clock maintained within primary microprocessor 114 may no longer be accurate. Accordingly, the real-time clock maintained within safety microprocessor 118 may be used to reset the real-time clock maintained within primary microprocessor 114.

A number of implementations have been described. Nevertheless, it will be understood that various modifications may be made. Accordingly, other implementations are within the scope of the following claims.

What is claimed is:

1. An infusion pump assembly comprising:
   a housing;
   a reservoir assembly disposed within the housing and configured to contain an infusible fluid;
   a motor assembly disposed within the housing and configured to act upon the reservoir assembly and dispense at least a portion of the infusible fluid contained within the reservoir assembly;
   processing logic disposed within the housing and configured to control the motor assembly;
   a primary power supply disposed within the housing and configured to provide primary electrical energy to at least a portion of the processing logic; and
   a backup power supply disposed within the housing and configured to provide backup electrical energy to the at least a portion of the processing logic in the event that the primary power supply fails to provide the primary electrical energy to the at least a portion of the processing logic;
   wherein the processing logic includes one or more circuit partitioning components configured to divide the processing logic into primary processing logic and backup processing logic; and
   wherein the one or more circuit partitioning components includes one or more of a diode assembly and a current limiting assembly.

2. The infusion pump assembly of claim 1 wherein the primary power supply includes a first battery.

3. The infusion pump assembly of claim 1 wherein the backup power supply is a super capacitor assembly.

4. The infusion pump assembly of claim 1 wherein the primary processing logic includes a primary microprocessor.

5. The infusion pump assembly of claim 1 wherein the backup processing logic includes a safety microprocessor.

6. The infusion pump assembly of claim 1 wherein the diode assembly is configured to allow the primary power supply to charge the backup power supply while prohibiting the backup power supply from providing backup electrical energy to the primary processing logic in the event that the primary power supply fails to provide the primary electrical energy to the primary processing logic.

7. The infusion pump assembly of claim 1 wherein the current limiting assembly is configured to limit the amount of the primary electrical energy available to charge the backup power supply.

8. The infusion pump assembly of claim 1 wherein the primary power supply is configured to provide electrical energy to one or more subsystems included within the infusion pump assembly.

9. The infusion pump assembly of claim 1 wherein the primary power supply and the backup power supply are configured to provide electrical energy to an audio system included within the infusion pump assembly.

10. The infusion pump assembly of claim 9 wherein the audio system is configured to provide an escalating alarm sequence in the event of a loss of a beacon signal, wherein the escalating alarm sequence includes at least a low-intensity alarm and a high-intensity alarm.

11. An infusion pump assembly comprising:
    a housing;
    a reservoir assembly disposed within the housing and configured to contain an infusible fluid;
    a motor assembly disposed within the housing and configured to act upon the reservoir assembly and dispense at least a portion of the infusible fluid contained within the reservoir assembly;
    processing logic disposed within the housing and configured to control the motor assembly;
    a first battery disposed within the housing and configured to provide primary electrical energy to at least a portion of the processing logic; and
    a super capacitor assembly disposed within the housing and configured to provide backup electrical energy to the at least a portion of the processing logic in the event that the first battery fails to provide the primary electrical energy to the at least a portion of the processing logic;
    wherein the processing logic includes one or more circuit partitioning components configured to divide the processing logic into primary processing logic and backup processing logic.

12. The infusion pump assembly of claim 11 wherein the primary processing logic includes a primary microprocessor.

13. The infusion pump assembly of claim 11 wherein the backup processing logic includes a safety microprocessor.

14. The infusion pump assembly of claim 11 wherein the one or more circuit partitioning components includes one or more of a diode assembly and a current limiting assembly.

15. An infusion pump assembly comprising:
    a housing;
    a reservoir assembly disposed within the housing and configured to contain an infusible fluid;
    a motor assembly disposed within the housing and configured to act upon the reservoir assembly and dispense at least a portion of the infusible fluid contained within the reservoir assembly;
    processing logic disposed within the housing and configured to control the motor assembly;
    a primary power supply disposed within the housing and configured to provide primary electrical energy to at least a portion of the processing logic; and
    a backup power supply disposed within the housing and configured to provide backup electrical energy to the at least a portion of the processing logic in the event that the primary power supply fails to provide the primary electrical energy to the at least a portion of the processing logic;

wherein the processing logic includes one or more circuit partitioning components configured to divide the processing logic into primary processing logic and backup processing logic.

16. The infusion pump assembly of claim 15 wherein the primary power supply includes a first battery.

17. The infusion pump assembly of claim 15 wherein the backup power supply is a super capacitor assembly.

18. The infusion pump assembly of claim 15 wherein the primary processing logic includes a primary microprocessor.

19. The infusion pump assembly of claim 15 wherein the backup processing logic includes a safety microprocessor.

20. The infusion pump assembly of claim 15 wherein the one or more circuit partitioning components includes one or more of a diode assembly and a current limiting assembly.

21. The infusion pump assembly of claim 20 wherein the diode assembly is configured to allow the primary power supply to charge the backup power supply while prohibiting the backup power supply from providing backup electrical energy to the primary processing logic in the event that the primary power supply fails to provide the primary electrical energy to the primary processing logic.

22. An infusion pump assembly comprising:
a housing;
a reservoir assembly disposed within the housing and configured to contain an infusible fluid;
a motor assembly disposed within the housing and configured to act upon the reservoir assembly and dispense at least a portion of the infusible fluid contained within the reservoir assembly;
processing logic disposed within the housing and configured to control the motor assembly and configured to generate an alarm control signal;
an RS232 line driver circuit coupled to the processing logic and configured to receive the alarm control signal and generate an alarm output signal based, at least in part, upon the alarm control signal;
an audio driver assembly coupled to the RS232 line driver circuit and configured to receive the alarm output signal and generate an audible alarm signal based, at least in part, upon the alarm output signal;
a primary power supply disposed within the housing and configured to provide primary electrical energy to at least a portion of the processing logic; and
a backup power supply disposed within the housing and configured to provide backup electrical energy to the at least a portion of the processing logic in the event that the primary power supply fails to provide the primary electrical energy to the at least a portion of the processing logic;
wherein the processing logic includes one or more circuit partitioning components configured to divide the processing logic into primary processing logic and backup processing logic.

23. The infusion pump assembly of claim 22 wherein the audio driver assembly includes a Piezo electric diaphragm.

* * * * *